(12) United States Patent
Caron

(10) Patent No.: US 8,210,045 B2
(45) Date of Patent: Jul. 3, 2012

(54) CONTINUOUS LASER GENERATION OF ULTRASOUND

(75) Inventor: James N. Caron, Silver Spring, MD (US)

(73) Assignee: James N. Caron, Silver Spring, MD (US)

( * ) Notice: Subject to any disclaimer, the term of this patent is extended or adjusted under 35 U.S.C. 154(b) by 381 days.

(21) Appl. No.: 12/547,469

(22) Filed: Aug. 25, 2009

(65) Prior Publication Data

US 2011/0048135 A1     Mar. 3, 2011

(51) Int. Cl.
*G01N 29/34* (2006.01)

(52) U.S. Cl. ............................................ 73/643; 73/597

(58) Field of Classification Search .................. 73/643, 73/597, 655
See application file for complete search history.

(56) References Cited

U.S. PATENT DOCUMENTS

| | | | | |
|---|---|---|---|---|
| 5,103,676 A | * | 4/1992 | Garcia et al. | 73/597 |
| 5,124,640 A | * | 6/1992 | Chern | 324/224 |
| 5,801,312 A | * | 9/1998 | Lorraine et al. | 73/602 |
| 6,182,512 B1 | * | 2/2001 | Lorraine | 73/655 |
| 6,590,647 B2 | * | 7/2003 | Stephenson | 356/301 |
| 6,699,192 B2 | * | 3/2004 | Ogawa | 600/437 |
| 7,464,596 B2 | * | 12/2008 | Bui et al. | 73/618 |
| 7,671,325 B2 | * | 3/2010 | Sanders et al. | 250/227.18 |
| 7,728,979 B2 | * | 6/2010 | Wang et al. | 356/445 |

* cited by examiner

*Primary Examiner* — J M Saint Surin

(57) ABSTRACT

A new invention for the laser-based generation of ultrasound is described. In conventional laser-based ultrasound, a pulse of light is incident on a solid. The light is converted to heat expanding the material near the surface. This thermoelastic expansion creates an acoustic wave in the material. Detection of the ultrasound allows the nondestructive inspection of the material. The rate of performing an ultrasound scan is inherently limited by the pulse rate of the laser. In this invention, a continuous wave (cw) high-power laser sweeps across the material, using thermoelastic expansion to create an ultrasound wavefront on the surface of and in the material. Detection of the ultrasound wavefront provides evidence of the strength of the material and the presence of defects. With Continuous Laser Generation of Ultrasound, material analysts will be able to perform ultrasound scans potentially hundreds of times faster than the current methods.

13 Claims, 6 Drawing Sheets

Conceptual drawing for the implementation of Continuous Laser Generation of Ultrasound. The optical beam 2 from a high-power continuous laser 1 is directed to a scanning mirror 3. The mirror rotates, controlled electronically, sweeping the beam along a line across the sample 5. This action creates ultrasound 4 in the material that can be used for nondestructive evaluation of the material properties.

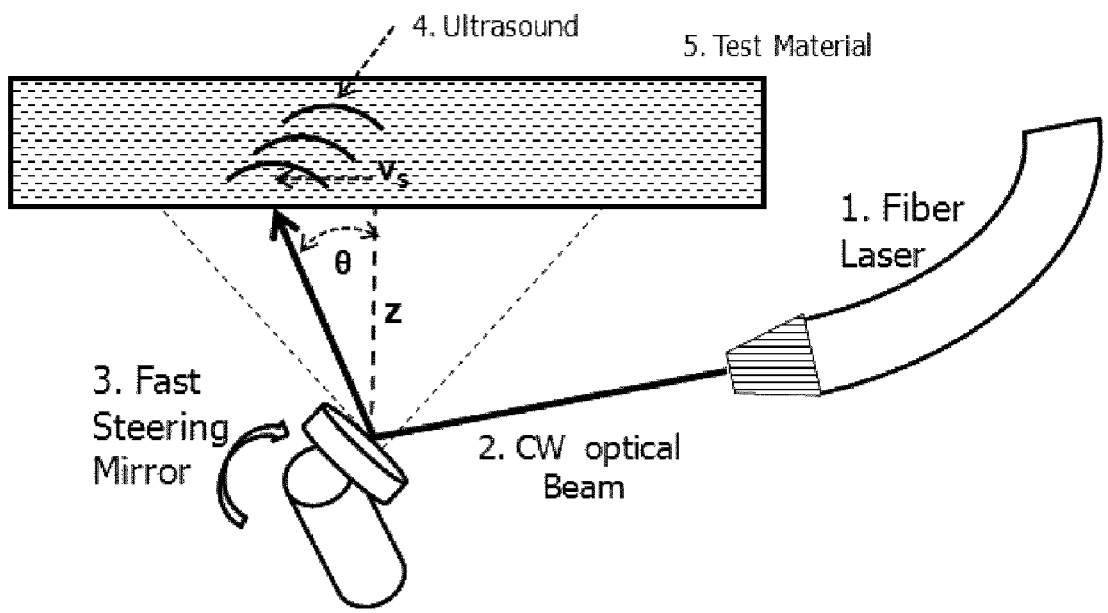

Figure 1: Conceptual drawing for the implementation of Continuous Laser Generation of Ultrasound. The optical beam 2 from a high-power continuous laser 1 is directed to a scanning mirror 3. The mirror rotates, controlled electronically, sweeping the beam along a line across the sample 5. This action creates ultrasound 4 in the material that can be used for nondestructive evaluation of the material properties.

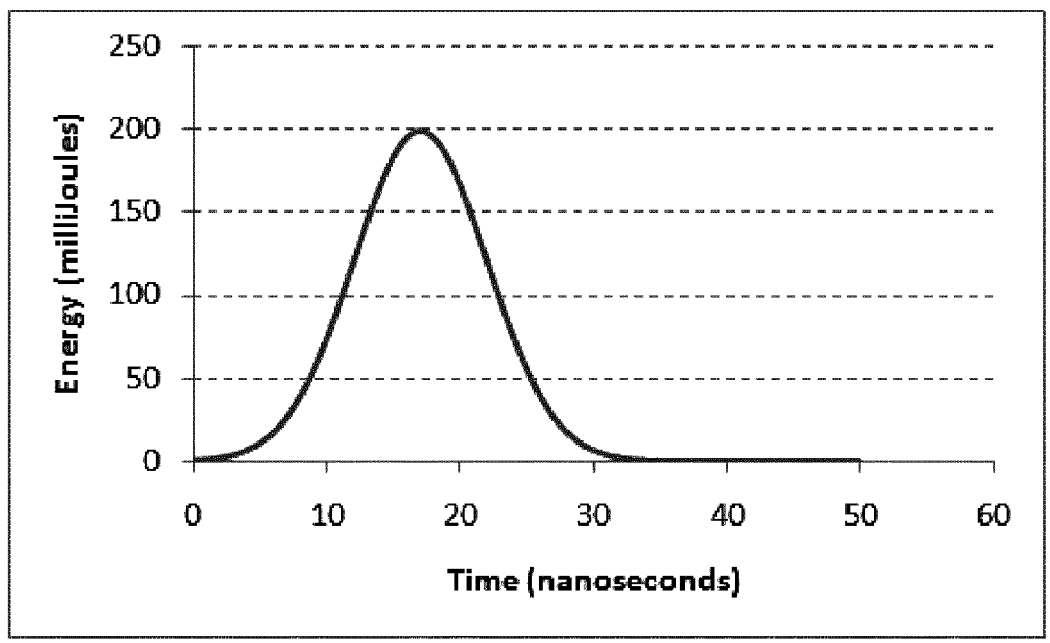
Figure 2: A Gaussian distribution curve that is used to simulate the time profile of a laser pulse. The x-axis is time in nanoseconds whereas the y-axis is energy. The pulse has a width at half the maximum value of 15 nanoseconds.

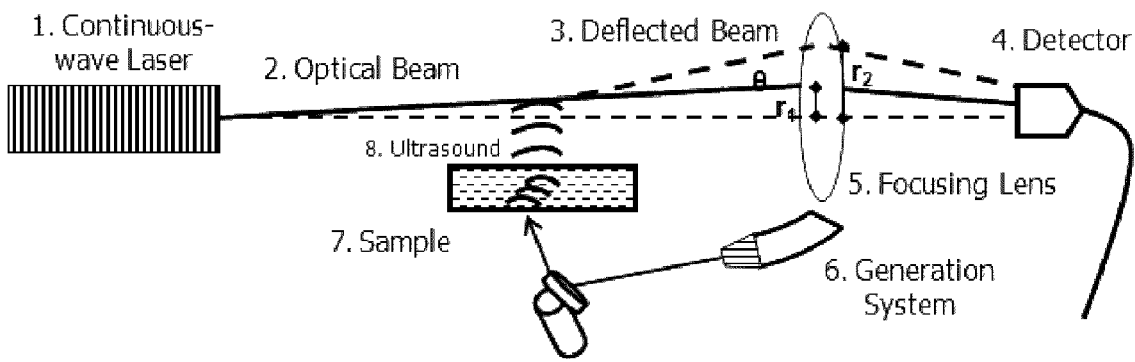

Figure 3: Arrangement for the sensing of ultrasound created by a CLGU 6 using Gas-coupled laser acoustic detection. Ultrasonic waveforms 8, upon transmission through the material 7, radiate an airborne wave. This modulates the index of refraction transverse to the probe beam 2 and causes a change in the direction of the optical beam path 3. The change is detected by a position-sensitive photodetector 4.

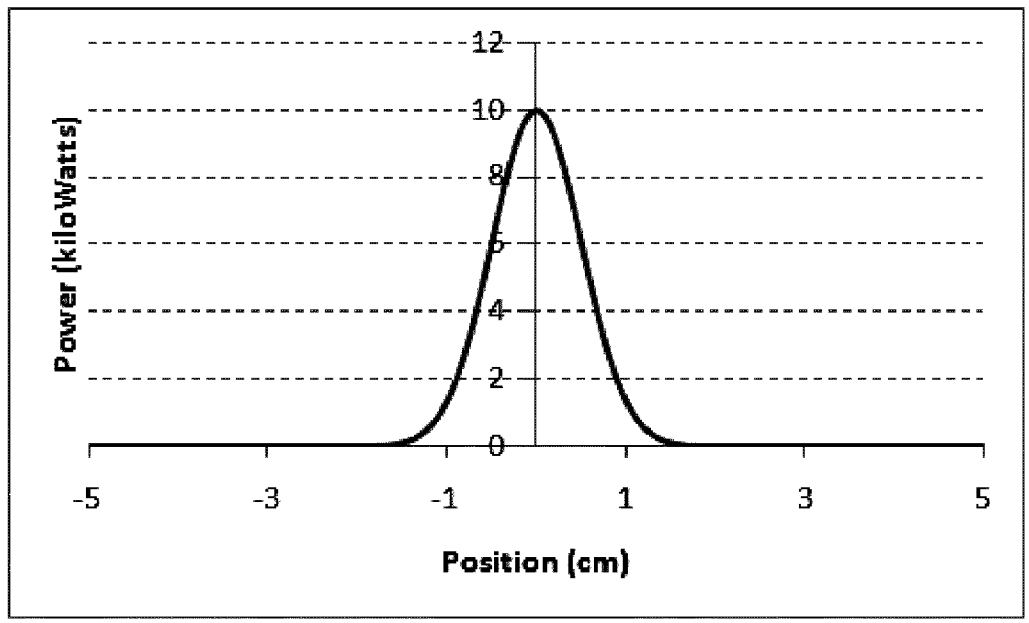
Figure 4: A Gaussian profile that simulates the power distribution of a ideal continuous laser. The x-axis is in centimeters and the y-axis shows the power. This beam would have a width at half the maximum value of about 2 centimeters.

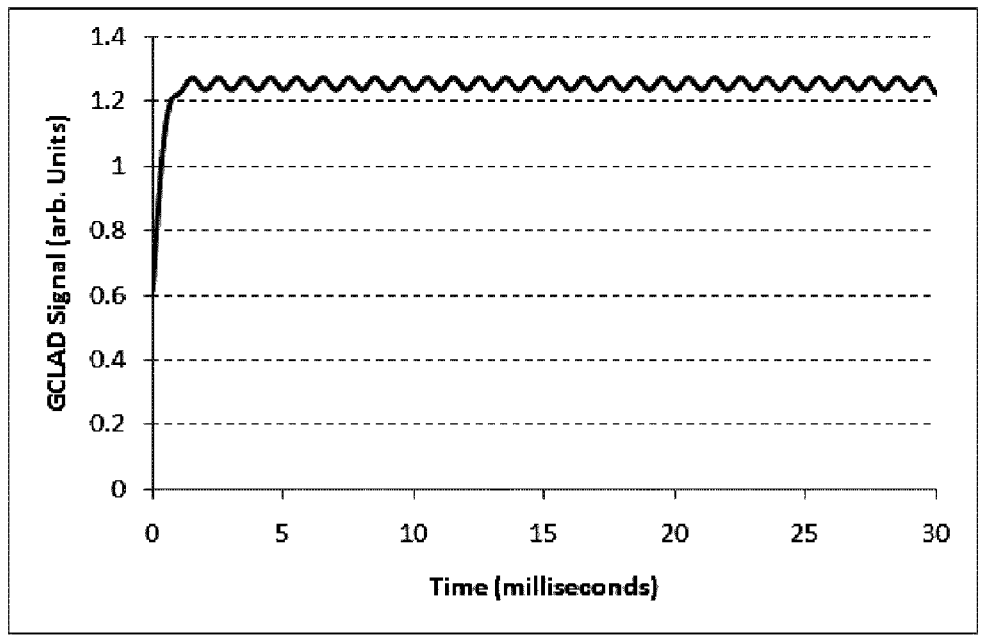
Figure 5: When the material is swept by the laser, each point gives rise to a Gaussian-type curve. The summation of all curves as a function of time simulates the signal received by a GCLAD detection system. This graph was created using Equation 4 and the laser profile of Figure 3. It is essentially the sum of 30 waveforms separated by 1 ms each.

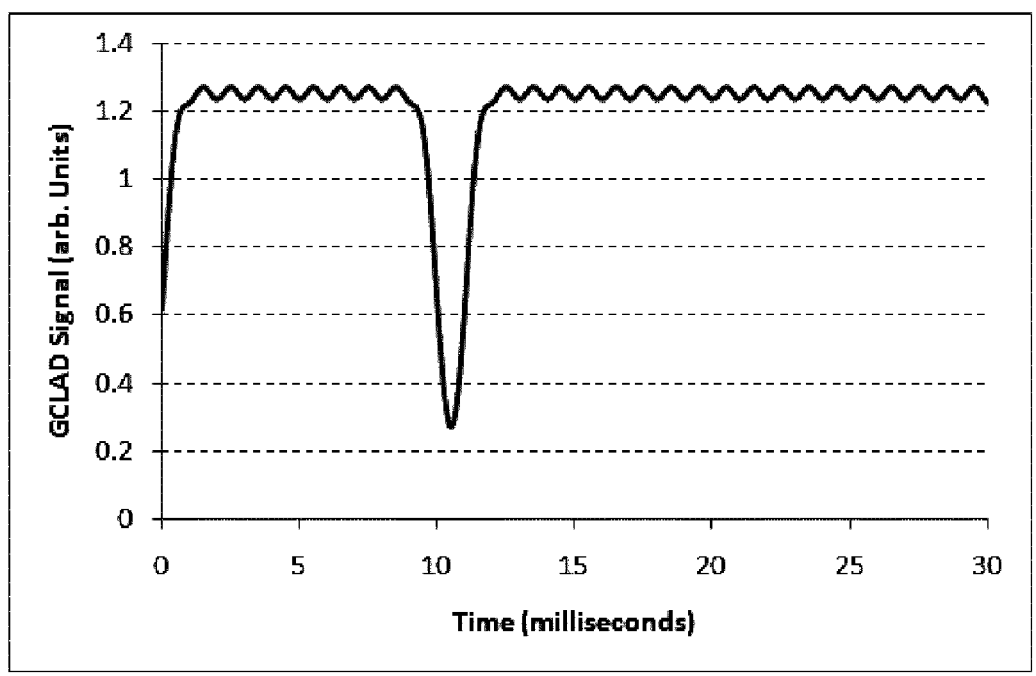
Figure 6: This graph shows the effect of a defect in the signal. Removing the tenth term, as described by equation 5, is similar to the response of the material to a defect located 10 cm from the start of the scan.

CONTINUOUS LASER GENERATION OF ULTRASOUND

BACKGROUND OF THE INVENTION

U.S. Pat. No. 4,966,459 discloses a method of detecting broadband ultrasound from materials using a confocal Fabry-Perot interferometer.

U.S. Pat. No. 6,041,020 discloses a method of detecting ultrasound using a cw laser to sense airborne ultrasound radiated from materials.

U.S. Pat. No. 6,484,052 discloses a method where pulsed laser-generated ultrasound is used to enhance the delivery of therapeutic compounds.

U.S. Pat. No. 6,668,654 discloses a method of dividing the laser pulse into spikes such that the generated ultrasound has a particular shape.

U.S. Pat. No. 6,833,554 discloses a method for pulsed generation and optically detecting shear waves in materials.

U.S. Pat. No. 6,809,991 discloses a method that selects an excitation signal, transmits, and detects the signal in an opaque solid, as in the detection of land mines.

U.S. Pat. No. 7,117,134 discloses a method to optimize the laser generation of ultrasound to improve the accuracy of the testing.

U.S. Pat. No. 7,278,315 discloses a laser-ultrasonic method to detect subsurface defects in using Rayleigh waves.

U.S. Pat. No. 7,474,411 discloses a method to optimize the laser generation of ultrasound to improve the accuracy of the testing.

U.S. Pat. No. 7,516,662 discloses a method where railway tracks are inspected using pulsed laser generation of ultrasound in the rails and detected by a cw laser with an optical interferometer U.S. Published Application 2004/0003662 discloses a similar method to U.S. Pat. No. 7,516,662 except that detection is performed with an air-coupled transducer.

DESCRIPTION

Background

Nondestructive evaluation of materials provides industrial and military entities with techniques that allow the inspection of products without damaging the material. Ultrasound is a well-known and conventional method of sensing the strength of materials and for searching for material defects. Typically, piezoelectric transducers generate and detect the acoustic waves in the material. To avoid the application of couplant gels, or under-water immersion, laser-based systems are being used to generate and detect the ultrasound in place of contact transducers.

In a typical laser-based ultrasound system, a pulsed laser is used to generate the ultrasound through a process called thermoelastic expansion. Detection can be accomplished using air-coupled transducers, a laser interferometer that senses surface motion, or a laser-based air-coupled optical beam deflection. The largest laser-based ultrasound (LU) system has been developed by Lockheed Martin (Dubois 2008) to inspect the wings and various parts of fighter aircraft. Several companies now sell smaller laser-based ultrasound systems that can be used on production lines, in research, and to inspect small parts.

PRIOR ART

When a laser pulse impacts an opaque material, part of the pulse is reflected and part is absorbed. Absorbed light energy is converted to thermal energy on the time scale of picoseconds (Spicer 1991), creating a thermoelastic expansion. This rapid expansion produces an acoustic wave that travels through the material. Several wave types are created simultaneously: longitudinal or compression waves, transverse or shear waves, surface acoustic waves (Rayleigh waves) in thicker plates and Lamb waves in thinner plates.

The efficiency of conversion from laser light to an acoustic wave depends on many factors, including surface reflectivity for the specified laser wavelength (Dubois 1993), temporal shape and duration of the laser pulse, (Enguehard 1997) energy of the laser pulse, and the surface area illuminated by the laser spot. Given that the choice of laser is usually governed by economical constraints, the flexibility in laser generation of acoustic waves mainly lies in the laser energy and pulse width. Purely thermoelastic generation is limited at higher intensities by the onset of surface vaporization, called ablation. (Caron 1996) Either increasing the laser energy, or decreasing the surface area illuminated by the pulse by focusing the beam, increases the power density. The proportionality of laser power density and acoustic amplitude has been derived in theory (White 1963) and demonstrated empirically (Caron 1996, Dewhurst 1982).

Many methods have been proposed to increase the efficiency of laser ultrasonic generation by spreading out the laser energy over a larger area. The use of a larger laser spot size allows the material to absorb more of the laser energy without surpassing the ablation threshold. The influence of laser energy distribution on efficiency of laser-generated ultrasound has been studied by Gonthier et al. (Gonthier 1994). Laser array sources have been implemented and described by Wagner et al. (Wagner 1990), Yang et al. (Yang 1993), Noroy et al. (Noroy 1993), and Steckenrider et al. (Steckenrider 1995). A holographic fringe generating spot was presented in von Gutfeld et al. (von Gutfeld 1983). Splitting a beam temporally by rapidly Q-switching a pulsed laser has also been shown to be an effective means of spreading the pulse power (Wagner 1990). The energy of the laser beam can be reduced by inserting beam attenuators (partially reflecting mirrors which divert a portion of the energy to beam dumps) or by reducing the amount of voltage supplied to the flash pump of the laser (Caron 1996).

Ultrasound measurements are usually classified as A, B, and C-scans. An A-scan is a single point measurement, and a B-scan is a measurement along a single line. A C-scan is an area scan where the laser generation and detection points are rastered across the surface of the sample. Alternatively, the lasers can be fixed while the material is moved by robotic arms. An important limiting factor when performing C-scans is the repetition rate of the laser. Pulsed lasers with suitable power and pulse rates operate in the range of 10 to 100 shots per second. To scan a 1 meter by 1 meter area, with a resolution of 1 mm at 100 Hz would take close to three hours. The invention described here can perform the same scan much faster.

SUMMARY OF THE INVENTION

Pulsed lasers are used for ultrasound generation since the rapid heating produces a thermoelastic expansion in the material. The expansion creates ultrasonic waveforms in the material that can be detected for the purpose of nondestructive evaluation. Here we describe an alternative method, designated Continuous Laser Generation of Ultrasound (CLGU). As pictured in FIG. 1, a continuous-wave (cw) laser is directed to a scanning mirror (or other scanning device). As it swivels, the mirror sends the optical beam along a line on the sample. The leading edge of the scanning beam creates the preferred rise time for the thermoelastic expansion in the material. The leading edge waveform combines with previous ones to form what can be called a wavefront to propagate through the material. As with pulsed laser generation of ultrasound (PLGU), CLGU creates several waveforms, including longitudinal, transverse, and surface waves. Measurements of these wave components provide the necessary values to calculate the strength of the material and locate defects.

The main advantage of CLGU over PLGU is the scanning rate. The scanning rate of pulsed lasers is limited by the repetition rate of the lasers. Typical pulsed lasers used for generation operate between 10 and 100 shots per second. To scan a 1 meter line with 0.1 cm resolution, the 100 Hz pulsed laser requires 10 seconds. As described below, the scanning rate of CLGU using a commercially available Fiber Laser is less than 10 milliseconds. Additionally, the scanning rate can be easily changed to enable the creation of waveforms with different frequency ranges, allowing different-sized defects to be isolated.

FIELD OF INVENTION

This invention relates to methods of producing acoustic waves in materials using light in order to determine strength, porosity, location of defects or other physical characteristics of the material.

BRIEF DESCRIPTION OF THE DRAWINGS

FIG. 1: Conceptual drawing for the implementation of Continuous Laser Generation of Ultrasound.

FIG. 2: A Gaussian distribution curve that is used to simulate the time profile light emitted by a pulsed laser.

FIG. 3: Arrangement for the sensing of laser-generated ultrasonic waveforms using GCLAD.

FIG. 4: A Gaussian profile that simulates the power distribution of a ideal continuous laser.

FIG. 5: The summation of all curves as a function of time simulates CLGU as detected by a GCLAD detection system.

FIG. 6: This graph shows the effect on the CLGU waveform caused by a defect (such as a void) in the material.

DETAILED DESCRIPTION OF THE INVENTION

Continuous-Wave Laser Generation

Concept

The shape of the laser pulse in time is approximately Gaussian, as shown in FIG. 2. Past research (Spicer 1991) has shown that ultrasound is formed in a solid within picoseconds of being struck by the laser. This creates a rapid expansion of the material that is dependent on the shape of the pulse. Following the pulse, the surface material loses its heat through thermal conductivity. By comparison, the thermal conductivity process is much slower than the thermal absorption, on the order of milliseconds for a millimeter thickness. (UMD) Therefore, the ultrasound wave is primarily created by the front surface rise time of the Gaussian pulse.

With current methods, this expansion is always created using a pulsed laser with pulse widths ranging from 5 to 50 nanoseconds. Ultrasound waves can potentially be created by a high-power continuous laser that is swept across the surface. The speed of the laser across the surface provides the necessary rise time to create the thermoelastic expansion. The power of the laser determines the amplitude of the waveform. Recently, high power cw lasers have been developed for welding purposes. (IPG) These lasers have sufficient power to create ultrasound using the CLGU method.

A simple analogy is to consider how waves can be created in a still tank of water. One can poke a finger into the pool to create waves that circle out, and waves that propagates down into the water. This resembles the reaction of a material to a pulsed laser. Another approach is to pull the finger along a line in the water, simulating CLGU. This will create waves on the surface that propagate outward, perpendicular to 'scan line'. Since, the finger also pushes water downwards, waves also propagate down into the water.

As with pulsed lasers, detection of the continuously-generated waveforms provides information about material strength, its porosity, and allows for the location of defects.

Scanning Rate

Laser ultrasound is typically carried out to image subsurface features or defects in materials. The size of the feature that can be resolved by ultrasound is related to the ultrasound frequency. A rule of thumb in industrial inspections is that ultrasound sensors can detect discontinuities that are larger than one-half the size of wavelength. Thus, an ultrasound wave with a frequency of 1 MHz in a material with a speed of sound of 1 mm/μs can detect defects as small as 0.5 mm.

For pulsed laser generation, the rise time of the pulse determines the frequency range of the ultrasound for a given material. Previous research has shown how the frequency components of a laser-generated ultrasound pulse changes with the temporal pulse width of the laser pulse. (Enguehard 1997, McDonald 1990) For CLGU, the frequency of the ultrasound is determined by the scan rate and power density of the laser beam.

IPG Photonics (IPG) is the largest producer of Yb-fiber lasers and develops fiber lasers with outputs of 1, 3, 5, 10, and 20 kWatts. These lasers, made for welding applications, plug into standard wall plugs and offer turn-key operation. A typical beam at output has an approximate spot size of 1 mm, producing a power density of about 0.32 MegaWaits per centimeter squared.

From past research, we know ablation sets in at about 60 $MW/cm^2$ for graphite-reinforced composite materials. Well-resolved waveforms can be generated and detected with a GCLAD system at 21 $MW/cm^2$. (Caron 1998) These pulses had a width of 5 nanoseconds. Thus, the amount of energy deposited to create the ultrasound was 0.1 Joules.

The 'linger' time required for a 10 kW fiber laser to deposit this much energy is about 10 microseconds. This produces an ultrasound frequency of 0.1 MHz, which is sufficient to sense cracks as small as 5 mm. The scanning rate can be estimated by the laser traversing a 1 mm spot for 10 microseconds, or a rate of 100 m/s. If the scanning mirror is located 1 m from the sample, the angular rate must be on the order of 45 degrees/millisecond.

Detection

Once the ultrasound has propagated through the material, a sensor must detect its presence on the surface. Detection can take the form of through-transmission or pulse echo. With through-transmission, the ultrasound generator and detector are on opposite sides of the material, detecting a waveform that has made one pass through the material. With pulse-echo, the generator and detector occur on the same side of the sample.

There are three possible detection methods, area, line, and point. Point detection, where a single data point is capture at a time, is the typical method used for laser ultrasonics. Contact transducers can be used, but generally an optical detection method is used. Different interferometers have been used, including heterodyne (two beam), (Wagner 1990, Scruby 1990) confocal Fabry-Perot, (Monchalin 1985), and photo-refractive quantum wells. (Lahiri 1998) A probe laser beam is directed to the detection point on the sample. The reflected light is gathered in an interferometer and sensed by a photodetector The surface displacement caused by the ultrasound changes the interference of the light, which creates the signal. The detection point can be on the same side as the generation laser (pulse-echo) or the opposite side (through transmission).

An area capture is similar to taking a photograph, where all data points are captured simultaneously. These systems have been created using piezoelectric arrays (Wygant 2005) and optical arrays (Yang 2008), but are used sparingly.

With this invention, the best detection technique may be line detection. The prime candidate is Gas-coupled Laser Acoustic Detection or GCLAD. Airborne ultrasound can be sensed by directing a laser beam through the acoustic disturbance. The disturbance causes a change in the optical path of the beam that can be detected with a position-sensitive photodetector; a technique designated gas-coupled laser acoustic detection (GCLAD). (Caron 2001, Caron 1998A, Caron 2000) One such disturbance is the radiation of an ultrasound wave from the surface of a sample, generated with either a pulsed laser or ultrasound transducer. As shown in FIG. 3, the probe beam passes parallel to the surface with a standoff distance that has ranged between 1 mm and 3 cm.

Since the beam can detect an airborne ultrasound wave at any point along its length (with varying sensitivity), GCLAD is a line detection method. The signal produced by CGLU/GCLAD will be a superposition of all generated wave forms, referred to as a convolution. Large defects in the sample will create large dips in the signal. The time of the dip can be calibrated to pinpoint the location of the defect on the sample. To detect smaller defects, some means of deconvolution can be considered. One can also envision modulating the generating beam to create an artificial frequency component in the signal.

EXAMPLE

The shape of the wavefront can be complicated, depending on the spread of the laser beam, the rate of scanning, and the thermoelastic interaction with the material. The simplest model is to assume the generated waveform has the temporal shape of the laser interaction. Using this model, we can estimate the shape of the detected waveform.

The static spatial shape of a good quality cw laser is very close to a Gaussian, $$P(x) = P_o e^{-\frac{x^2+y^2}{\omega^2}} \quad (1)$$

where $\omega$ is the width and the beam is centered at position x=0, y=0, as shown in FIG. 4. Steering the beam along a line on the surface, at a speed of $v_s$ produces $$P(x, t) = P_o e^{-\frac{(x+\omega-v_s t)^2+y^2}{\omega^2}} \quad (2)$$

In deposited power. To first order approximation, the received GCLAD signal S(t) will be an integration of the deposited power, $$S(t) = S_o \int_y \int_x P_o e^{-\frac{(x+\omega-v_s t)^2+y^2}{\omega^2}} dx dy \quad (3)$$

where $S_o$ is calibration factor taking into account the sensitivity of the detection system. This can be approximated by a superposition $$S \propto \sum_x e^{-\frac{(x+\omega-v_s t)^2}{\omega^2}} \quad (4)$$

as shown in FIG. 5. Laser-generated waveforms will be more complicated than this.

Using Equation 4, we can simulate the effect of a defect in the material by removing one term. Subtracting off the tenth term creates a defect at a distance of 10 cm from the start of the scan $$S \propto \sum_x e^{-\frac{(x+\omega-v_s t)^2}{\omega^2}} - e^{-\frac{(10+\omega-v_s t)^2}{\omega^2}}. \quad (5)$$

This is plotted in FIG. 6. The graph shows a large dip that starts at a time of 10 milliseconds. Since the scan rate is 1 cm/ms, the defect is located at 10 cm.

In addition to the wave propagating in the material, surface waves, operating as an ultrasonic 'wake', can also be measured. This allows Rayleigh and Lamb waves to be detected, providing further information about surface cracks, porosity and transverse strength. Continued research will show how the best possible information can be pulled from the wavefront. Modulating the laser source may also provide a means to enhance signal recovery by locking in on the modulation frequency using a lock-in amplifier.

Potential Applications

This invention can be used in many applications where laser-based ultrasound is applied. The inspection of materials for defects, both in processing, and after the material is in use, is the largest area of application. Scanning the composite materials designed for both military and commercial aircraft requires a fast and effective nondestructive evaluation. Laser Ultrasound is a prime candidate. Laser ultrasound has also been used to inspect paper, inspecting materials at elevated temperature, semiconductors, thin films, and more recently medical sensing.

The system described here will be used where the user requires a faster system. If used to determine the health of military aircraft, for example, a faster system would shorten the maintenance time between flights. For production lines, faster scanning could decrease the time of production. An optimum situation is where the product is being pulled under the scanning system. Thus, one dimension of the scanning is achieved by the CGLU whereas the second is by the moving part on the conveyor belt.

Conclusions, Ramifications, and Scope

Continuous Laser Generation of Ultrasound has several unique characteristics that are not provided by pulsed-laser generation. The main advantage is the speed of scanning. This will reduce inspection time without sacrificing the quality of information received. Increased scanning speed also allows the user to do finer scans without increased cost. This produces better ultrasound images with improved resolution.

Also, by changing scanning speed, the user can change the ultrasound frequency, allowing different sizes of defects to be found. Finally, coupled with a GCLAD system, the inspection system has matching line generation and line detection. So, where a pulsed system needs to be scanned in two dimensions, this invention only needs one.

Laser ultrasound systems are becoming more commonplace in industrial and military complexes. For Aerospace companies, more and more components are being built using composite materials. Many parts are formed by wrapping layers of the composite onto rotating mandrels. A CLGU/GCLAD system would be the ideal method to verify adherence for each layer as it is being formed. Using simple robotics, both new and aging airplane wings can be scanned for defects, much faster than before.

This invention will also spur research into this method. Higher powered lasers will enable even faster ultrasound scans. Researchers will develop existing or new signal processing techniques, like deconvolution and source separation, to extract material properties from the wavefront propagating into the material, and the wake propagating along the surface.

DETAILED DESCRIPTION OF THE DRAWINGS

FIG. 1: Conceptual drawing for the implementation of Continuous Laser Generation of Ultrasound. The optical beam from a high-power continuous laser is directed to a scanning mirror. The mirror rotates, controlled electronically, sweeping the beam along a line across the sample. This action creates ultrasound in the material that can be used for nondestructive evaluation of the material properties.

FIG. 2: A Gaussian distribution curve that is used to simulate the time profile of a laser pulse. The x-axis is time in nanoseconds whereas the y-axis is energy. The pulse has a width at half the maximum value of 15 nanoseconds.

FIG. 3: Arrangement for the sensing of laser-generated ultrasonic waveforms using GCLAD. Ultrasonic waveforms, upon transmission through the material, radiate an airborne wave. This modulates the index of refraction transverse to the probe beam and causes a change in the direction of the optical beam path. The change is detected by a position-sensitive photodetector.

FIG. 4: A Gaussian profile that closely resembles the power distribution of a ideal continuous laser. The x-axis is in centimeters and the y-axis shows the power. This beam would have a width at half the maximum value of about 2 centimeters.

FIG. 5: When the material is swept by the laser, each point gives rise to a Gaussian-type curve. The summation of all curves as a function of time simulates the signal received by a GCLAD detection system. This graph was created using Equation 4 and the laser profile of FIG. 3. It is essentially the sum of 30 waveforms separated by 1 ms each.

FIG. 6: This graph shows the effect of a defect in the signal. Removing the tenth term, as described by equation 5, is similar to the response of the material to a defect located 10 cm from the start of the scan.

REFERENCES (Dubois 2008) M. Dubois, T. Drake, and M. Osterkamp, "Low-Cost Ultrasonic Inspection of Composites for Aerospace Applications with LaserUT Technologies", *Journal of JSNDI*, Volume 57 Number 1, Japanese Society of Non-Destructive Inspection, pp. 11-18, 2008.

(Spicer 1991) J. B. Spicer, *Laser Ultrasonics in Finite Structures: Comprehensive Modelling with Supporting Experiment*, Ph.D. Thesis, Johns Hopkins University, 1991.

(UMD) Center for Advanced Life Cycle Engineering, University of Maryland, "Report on the Thermal Diffusivity, Specific Heat, and Thermal Conductivity of Aluminum Oxide and Pyroceram," htttp://www.calce.umd.edu/general/Facilities/laser_flash/Results.pdf.

(Dubois 1993) M. Dubois, M. Choquet, J. P. Monchalin, F. Enguehard, and L. Betrand, "Absolute Optical Absorption Spectra in Graphite Epoxy by Fourier Transform Infrared Photoacoustic Spectroscopy", *Optical Engineering*, Vol. 32, no. 9, p. 2255, 1993.

(Enguehard 1997) F. Enguehard and L. Bertrand, "Effects of optical penetration and laser pulse duration on laser generated longitudinal acoustic waves," *J. Appl. Phys.*, Vol. 82, p. 1532, 1997.

(Caron 1996) J. N. Caron, Y. Yang, J. B. Mehl, and K. V. Steiner, "Thermoelastic/Ablatic Generated Ultrasound in Graphite/Polymer Composites Detected with a CFP-based System in Reflection Configuration", *Review of Progress in Quantitative Nondestructive Evaluation*, Vol. 16, 1996.

(White 1963) R. M. White, "Generation of Elastic Waves by Transient Surface Heating," *Journal of Applied Physics*, Vol. 14, no. 12, p. 3559, 1963.

(Dewhurst 1982) R. J. Dewhurst, D. A. Hutchins, and S. B. Palmer, "Quantitative Measurements of Laser-Generated Acoustic Waveforms", *Journal of Applied Physics*, Vol. 53, no. 6, p. 4064, 1982.

(Gonthier 1994) J. C. Gonthier, M. Dubois, F. Enguehard, and L. Betrand, "Influence of the Pulse Energy Distribution on the Efficiency of Ultrasound Generation by Laser", *Journal De Physique IV*, Vol. 4, p. C7-685, 1994.

(Wagner 1990) J. W. Wagner, J. B. Deaton, J. B. Spicer, and A. D. W. McKie, "Laser Generation of Narrowband and Directed Ultrasound for Noncontact Ultrasound Testing", *IEEE Ultrasonics Symposium Proceedings*, Vol. 2, p. 661, 1990.

(Yang 1993) J. Yang, N. DeRidder, C. Ume, and J. Jarzynski, "Non-contact Optical Fibre Phased Array Generation of Ultrasound for Non-destructive Evaluation of Materials and Processes", *Ultrasonics*, Vol. 31, no. 6, p. 387, 1993.

(Noroy 1993) M. Noroy, D. Royer, and M. Fink, "The Laser-Generated Ultrasonic Phased Array: Analysis and Experiments," *Journal of the Acoustical Society of America*, Vol. 94, no. 4, p. 1934, 1993.

(Steckenrider 1995) J. S. Steckenrider, T. W. Murray, J. W. Wagner, and J. B. Deaton Jr., "Sensitivity Enhancement in Laser Ultrasonics using a Versatile Laser Array System," *Journal of the Acoustical Society of America*, Vol. 97, no. 1, p. 273, 1995.

(von Gutfeld 1983) R. J. von Gutfeld, D. R. Viglioth, C. S. Ih, and W. R. Scoff, "Thermoelastic Hologram for Focused Ultrasound," *Applied Physics Letters*, Vol. 42, no. 12, p. 1018, 1983.

(IPG) IPG Photonics Corporation, 50 Old Webster Road, Oxford, Mass. 01540.

(McDonald 1990) F. A. McDonald, "On the precursor in laser-generated ultrasound waveforms in metals," *Applied Physics Letters*, Vol. 56 (3), pp. 230-232, 1990.

(Caron 1998) J. N. Caron, Y. Yang, J. B. Mehl and K. V. Steiner, "Thermoelastic and Ablative Laser Generation of Ultrasonic Waveforms in Graphite/Polymer Composite Materials," non-published, available from http://www.quarktet.com/pdfs/Quarktet-TeAbGeninComposites.pdf, May 1998.

(Wagner 1990) Wagner, J. W., Optical Detection of Ultrasound, Physical Acoustics, Vol. 19, pp. 201-266 (1990).

(Scruby 1990) C. B. Scruby and L. E. Drain, *Laser Ultrasonics*, (Adam Hilger: Bristol), 1990.

(Monchalin 1985) J. P. Monchalin, "Optical Detection of Ultrasound at a Distance Using a Confocal Fabry-Perot Interferometer," *Applied Physics Letters*, Vol. 47, p. 14, 1985.

(Lahiri 1998) I. Lahiri, L. J. Pyrak-Nolte, D. D. Noltea, M. R. Melloch, R. A. Kruger, G. D. Bacher and M. B. Klein, "Laser-based ultrasound detection using photorefractive quantum wells," *Applied Physics Letters*, Vol. 73, p. 1041, 1998.

(Wygant 2005) I. O. Wygant, X. Zhuang, P. S. Kuo, D. T. Yeh, O. Oralkan, B. T. Khuri-Yakub, "Photoacoustic Imaging Using a Two-Dimensional CMUT Array," *Ultrasonics Symposium*, Vol. 4, issue 18-21, p. 1921, 2005.

(Yang 2008) Yang HOU 1, Jin-Sung KIM 1, Shai ASHKENAZI 2, Sheng-Wen HUANG 2, L. Jay GUO 1, Matthew ODONNELL 3, "Broadband All-Optical Ultrasound Transducer," 1*st International Symposium on Laser Ultrasonics,* 2008.

(Caron 2001) J. N. Caron, Y. Yang, J. B. Mehl, and K. V. Steiner, "Gas coupled laser acoustic detection for ultrasound inspection of composite materials", *Materials Evaluation*, Vol. 58, No. 5, pp. 667-671, 2001.

(Caron 1998A) J. N Caron, Y. Yang, J. B. Mehl and K. V. Steiner, "Gas-coupled Laser Acoustic Detection at Ultrasonic and Audible Frequencies," *Review of Scientific Instruments*, Vol. 69(8), pp. 2912-2917, 1998.

(Caron 2000) J. N Caron, Y. Yang, J. B. Mehl and K. V. Steiner, "Gas-coupled Laser Acoustic Detection," U.S. Pat. No. 6,041,020, Mar. 21, 2000.

What is claimed is:

1. A method of generating acoustic waves in materials, said material comprising the following steps: (a) providing a material; (b) sweeping the position of a continuous beam of light across said material at a predetermined sweep rate using one or more scanning devices; (c) continuously creating an acoustic wave on the surface of and in said material, resulting from absorption of said light by said material; and (d) using one or more sensors to detect said waveform.

2. The method of claim 1, wherein said providing step comprises providing said material in the form of a solid.

3. The method of claim 1, wherein said providing step comprises providing said material in the form of a liquid.

4. The method of claim 1, wherein said sweeping step comprises using a laser to create the light that is continuously moved across said material producing said acoustic wave.

5. The method of claim 1, further comprising modulating the power of said light beam to enhance signal recovery.

6. The method of claim 1, further comprising using said sweep rate of said light beam to adjust the frequency content of said acoustic wave.

7. The method of claim 1, further comprising using the signals from said sensors as a means to interrogate the strength and/or quality of said material.

8. The method of claim 1, further comprising using the signals from said sensors as a means to inspect said material for defects.

9. The method of claim 1, further comprising using the signals from said sensors to sense the material properties of an object.

10. The method of claim 1, further comprising using contact acoustic transducers to detect said acoustic wave.

11. The method of claim 1, further comprising using laser-based ultrasound detection to continuously detect said waveform.

12. The method of claim 1, further comprising producing an ultrasound image of said material from the detection of multiple acoustic waveforms.

13. The method of claim 1, further comprising said one or more scanning devices and said one or more sensors in an integrated automated ultrasound inspection system.

* * * * *